(12) United States Patent
Reick

(10) Patent No.: US 8,790,336 B2
(45) Date of Patent: Jul. 29, 2014

(54) NEUTRAL ELECTRODE DETECTION

(75) Inventor: Michael Reick, Ebersbach (DE)

(73) Assignee: Erbe Elektromedizin GmbH, Tübingen (DE)

( * ) Notice: Subject to any disclaimer, the term of this patent is extended or adjusted under 35 U.S.C. 154(b) by 1083 days.

(21) Appl. No.: 12/747,809

(22) PCT Filed: Dec. 12, 2008

(86) PCT No.: PCT/EP2008/010590
§ 371 (c)(1),
(2), (4) Date: Jun. 11, 2010

(87) PCT Pub. No.: WO2009/077132
PCT Pub. Date: Jun. 25, 2009

(65) Prior Publication Data
US 2010/0280512 A1    Nov. 4, 2010

(30) Foreign Application Priority Data

Dec. 14, 2007  (DE) .......................... 10 2007 060 431

(51) Int. Cl.
*A61B 18/16*    (2006.01)

(52) U.S. Cl.
USPC ............................................... 606/34; 606/35

(58) Field of Classification Search
CPC ........................................... A61B 2018/00875
USPC ........................................ 606/32, 34, 35, 41
See application file for complete search history.

(56) References Cited

U.S. PATENT DOCUMENTS

| | | | | |
|---|---|---|---|---|
| 4,754,757 | A | * | 7/1988 | Feucht ............................. 606/35 |
| 6,115,638 | A | * | 9/2000 | Groenke ......................... 607/142 |
| 6,165,169 | A | * | 12/2000 | Panescu et al. .................... 606/1 |
| 6,217,574 | B1 | | 4/2001 | Webster |
| 6,368,709 | B1 | | 4/2002 | Schleussner |
| 7,258,688 | B1 | | 8/2007 | Shah et al. |
| 8,624,606 | B2 | * | 1/2014 | Gilbert .......................... 324/649 |
| 2003/0055478 | A1 | * | 3/2003 | Lyster et al. ................... 607/142 |
| 2006/0074411 | A1 | * | 4/2006 | Carmel et al. ................... 606/32 |
| 2007/0049916 | A1 | * | 3/2007 | Isaacson et al. ................. 606/32 |

FOREIGN PATENT DOCUMENTS

| | | |
|---|---|---|
| DE | 42 32 255 C1 | 2/1994 |
| DE | 43 39 049 A1 | 5/1995 |
| EP | 0 981 449 A1 | 3/2000 |
| EP | 1 440 665 A1 | 7/2004 |
| WO | WO-97/24155 A1 | 7/1997 |

* cited by examiner

*Primary Examiner* — Michael Peffley
*Assistant Examiner* — Thomas Giuliani
(74) *Attorney, Agent, or Firm* — Dickstein Shapiro LLP

(57) ABSTRACT

A coded neutral electrode including at least two electrodes electrically insulated from each other and having active surfaces for application to a skin segment of a patient, and a cover film, having a known electrical resistance, removably attached to the active surfaces in such a way that the active surfaces are electrically connected to each other by means of the cover film, and an electrosurgical apparatus for use with the coded neutral electrode and methods of production and use of the coded neutral electrode.

8 Claims, 2 Drawing Sheets

NEUTRAL ELECTRODE DETECTION

FIELD OF THE DISCLOSED EMBODIMENTS

The disclosed embodiments relate to a coded neutral electrode, an electrosurgical apparatus for use with the neutral electrode, and methods for the production and use of such a neutral electrode.

BACKGROUND

With electrosurgical appliances, different instruments may be connected to a single electrosurgical apparatus. In order to adjust the electrosurgical apparatus to correspond to the connected instrument, it is disclosed, for example in DE 43 39 049 C2, that coding may be provided to the apparatus via a resistance that is present in the connected instrument and its electrical connection to the electrosurgical apparatus, such that the data on the connected instrument can be read from a reference list and the electrosurgical apparatus may be adjusted based on the identified connected instrument.

In many cases, monopolar instruments are used in electrosurgery, during which a neutral electrode is stuck onto a skin segment of a patient. Neutral electrodes of this kind are often equipped with two or more active surfaces to enable determination of the correct seating of the neutral electrode on the patient's skin segment. Neutral electrodes of this kind are used in an extremely wide variety of embodiments, depending upon what surfaces or surface sizes are required. For example, it is quite conceivable that neonatal surgery will require the use of different neutral electrodes than those used in operations on adult patients. This means that, depending upon the neutral electrode used, the operating parameters of the electrosurgical apparatus will need to be at least partially adjusted. This is not only labor-intensive, but there is also the risk that errors could occur, which, particularly in this field of technology, could have fatal consequences.

SUMMARY

The disclosed embodiments include a neutral electrode, an electrosurgical apparatus, and method for producing and putting into use a neutral electrode that allow for simplified operability and higher safety.

In a preferred embodiment, a cover film, which is already a component of a neutral electrode, used to package and sterilize the neutral electrode and to enable it to be adhered in sterile condition to the surface of a patient's skin, is used as a coding device, which can then be discarded after the coding of the electrosurgical apparatus. This arrangement allows for easier manufacturing of a neutral electrode with a coding device and significantly simplifies its use. These advantages, in turn, result in increased patient safety.

The cover film can be equipped with conductive sections (having low resistance), which are in contact with the electrodes when they are covered and provide defined resistances between them, e.g. as separate components. It is simpler to use material with a defined resistivity as the cover film. It is particularly simple and easily reproducible results are produced if the cover film is a homogeneous material whose electrical parameters are defined during production.

The electrosurgical apparatus includes a resistance-measuring device, which is used to measure the resistance between the electrically insulated electrodes, which is in turn defined by the adherent cover film.

In one embodiment, the measured resistance can be displayed for an operator to read so that the operator can use the value of the measured resistance to identify the neutral electrode that is being used and is able to adjust the electrosurgical apparatus accordingly. In another embodiment, operation may be simplified by including a decoding device that is used to compare the measured resistance with stored resistance values and, from the result of the comparison, to directly display the type of neutral electrode used, so the operator may adjust the electrosurgical apparatus according. In another embodiment, operation is even further simplified if the parameters corresponding to the connected neutral electrode are derived directly from the comparison result or the measured resistance and supplied to the electrosurgical apparatus.

The maximum current that flows through the neutral electrode and thus, the electrosurgical apparatus used on the patient is one parameter, which is preferably set by means of the described device in the electrosurgical apparatus. For example, the maximum current is limited to about 300 mA if a neutral electrode is used for an operation on new-born babies (neonatal surgery). Therefore, in such a case, by use of the disclosed embodiments, the maximum current limitation no longer has to be set by the operating staff; instead this setting may be performed automatically on the basis of the measured resistance values.

It is evident from the above that the disclosed embodiments also relate to the use of a plastic or ceramic film having a defined resistance, namely use as a cover film for a neutral electrode to cover the active surfaces thereof.

The disclosed embodiments also include a method of production and method of use of a neutral electrode.

The production method includes, producing a neutral electrode having at least two electrodes electrically insulated from each other and forming active surfaces for application to a patient's skin segment. The production method further includes attaching a cover film to the active surfaces using an adhesive layer such that the cover film remains adherent during the handling of the neutral electrode (during packaging and shipping) but can be removed prior to an operation. The cover film is formed of a material having a defined electrical resistance such that the active surfaces of the neutral electrode are connected to each other by the resistance. The production method further includes packaging and sterilizing the neutral electrode established and protected by the cover film.

The method of use of the neutral electrode includes, removing the neutral electrode from the packaging (at which point the neutral electrode is still covered by the cover film) and connecting the neutral electrode to an electrosurgical generator. Then, a measuring device is used to determine the resistance between the electrodes. Next, a high-frequency generator is adjusted in accordance with the resistance determined by the measuring device, since this resistance is characteristic of the connected neutral electrode. Once the high-frequency generator is appropriately adjusted, the cover film is removed so that the neutral electrode can be applied to the envisaged skin segment of a patient.

Preferably, the high-frequency generator is set in accordance with the measured resistance value, which is in accordance with the measured neutral electrode type, to a maximum current. This is particularly simple if the measured resistance value is compared with stored values each representing a certain neutral electrode type.

BRIEF DESCRIPTION OF THE DRAWINGS

The following describes an exemplary embodiment of the invention in more detail with reference to the attached diagrams.

DETAILED DESCRIPTION

Figure 1:
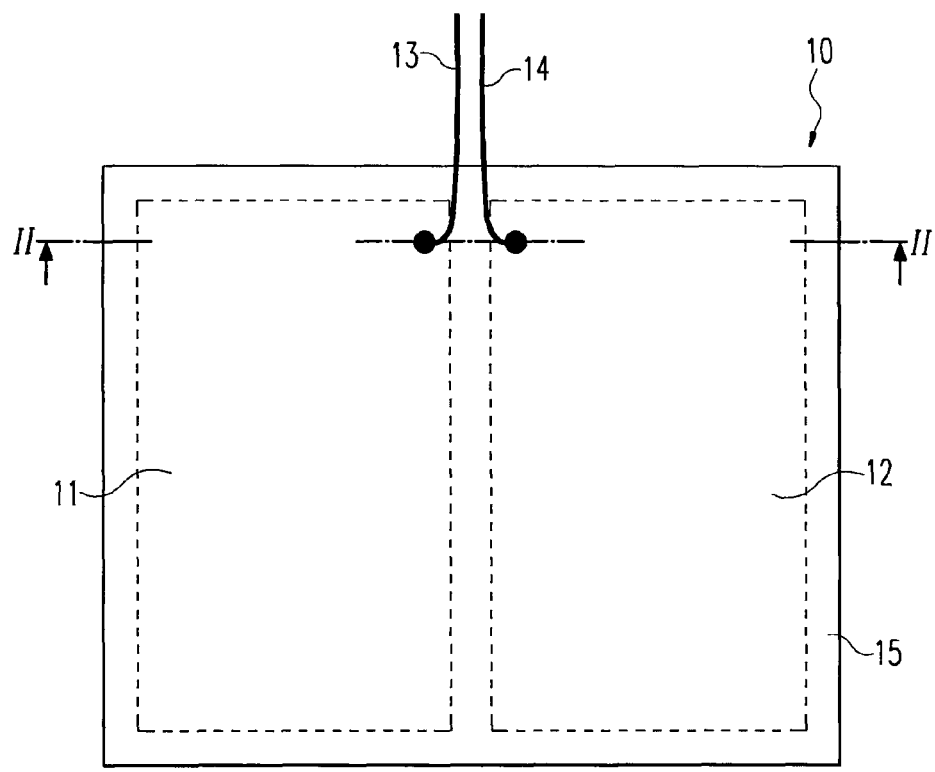
FIG. 1 illustrates a top view of the neutral electrode according to a disclosed embodiment.

In the following description, the same reference numerals denote the same parts or parts having similar functions.

Figure 2:
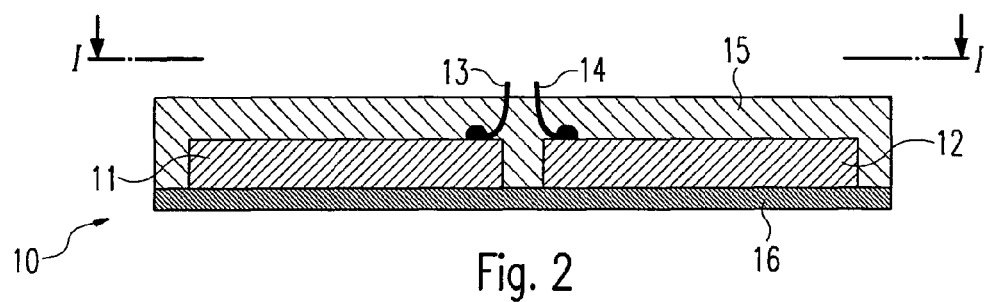
FIG. 2 is a cross-sectional view along the line II-II from FIG. 1.

As shown in FIGS. 1 and 2, the neutral electrode includes two generally metallic electrodes 11, 12, which are applied to a support 15 and firmly connected thereto. Before use, as shown FIG. 2, active surfaces of the electrodes 11, 12, which are not connected to the support or are covered by this are covered by a cover film 16. As indicated in FIG. 2, the cover film 16 can be made of a homogeneous material having a defined electrical resistance. However, it is also possible to use separate contacts with a resistance between them (which can in turn be embodied as a film) in order to create the defined resistance between the electrodes 13 and 14.

For connection to an electrosurgical apparatus, connection lines 13, 14 are provided, which are connected to the electrodes 11, 12 in an electrically conductive way.

Figure 3:
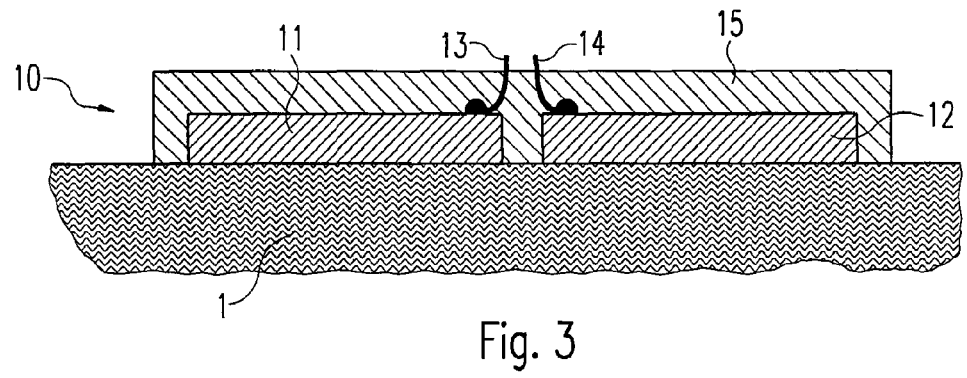
FIG. 3 is a representation similar to that in FIG. 2, but with a removed cover film and in glued-on condition.

For application to a skin segment 1 of a patient, the cover film 16, which is connected to the electrodes 11, 12 and part of the support 15 by an adhesive layer, is removed. After removal, the neutral electrode 10 can be adhered to the skin segment 1 of the patient or attached to this skin segment 1 in some other way, as shown in FIG. 3. Here, as known to those of skill in the art, a conductive gel is generally used in order to reduce the resistance between the electrodes 11 and 12 and the skin segment 1.

Figure 4:
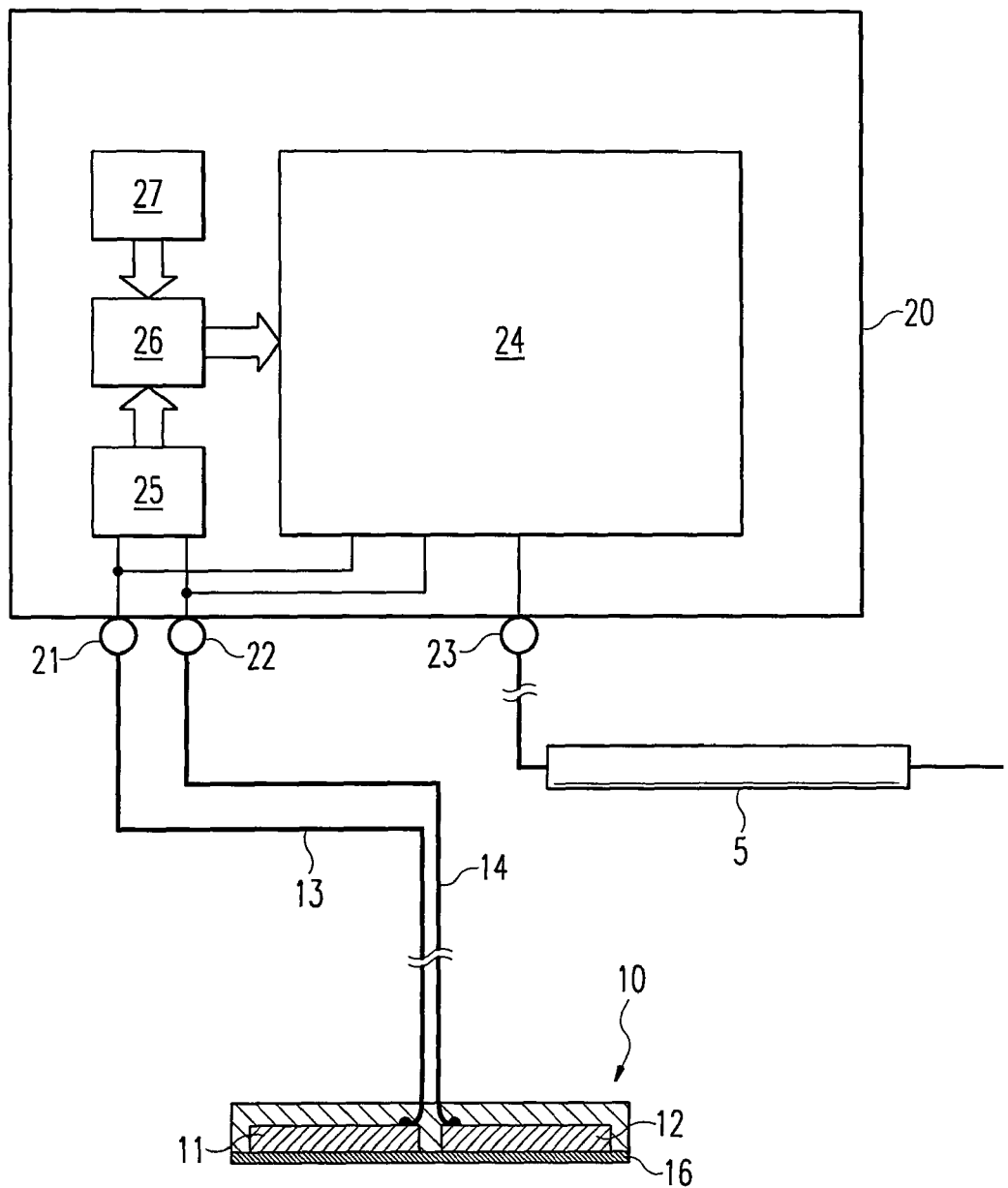
FIG. 4 is a schematic representation of the electrosurgical apparatus according to a disclosed embodiment in combination with the neutral electrode.

The electrosurgical apparatus according to a disclosed embodiment is shown schematically in FIG. 4 and identified with reference number 20.

The electrosurgical apparatus 20 includes connection terminals 21, 22 for the neutral electrode 10 and one (or more) terminal 23 for the connection of an electrosurgical instrument 5. These terminals 21-23 are connected to a high-frequency generator 24.

Also provided in the electrosurgical apparatus 20 is a resistance-measuring device 25, which is connected to the connection terminals 21 and 22 and, via the connection lines 13, 14 to the electrodes 11, 12 of the neutral electrode 10. The resistance-measuring device 25 (optionally an impedance measuring device) determines the degree of the electrical resistance between the two electrodes 11, 12 from a measured current flowing from one of the electrodes 11 through the electrically conductive cover film 16 to the other electrode 12. The resistance value determined is supplied by the resistance-measuring device 25 to a comparator 26, which compares the measured value with values stored in a memory 27. The stored values correspond to different embodiments of neutral electrodes 10. The comparison result is transmitted by the comparator 26 to the high-frequency generator 24 which thereupon sets working parameters. A working parameter of this kind is in particular a maximum current that can be delivered by the high-frequency generator, which is of extreme importance, in particular in the case of neonatal operations.

It should be pointed out here that all the above described parts and in particular the details illustrated in the drawings are essential for the disclosed embodiments alone and in combination. Adaptations thereof are the common practice of persons skilled in the art.

The invention claimed is:

1. An electrosurgical apparatus comprising an electrosurgical appliance and a neutral electrode connected thereto, the neutral electrode having at least two electrodes which can be applied to a skin segment of a patient and are electrically insulated from each other, and a cover film attached to active surfaces of the at least two electrodes, wherein the cover film is removable prior to application to the patient and the cover film has a known resistance so that a defined resistance is created between the active surfaces of the at least two electrodes, the electrosurgical appliance comprising:
   a resistance-measuring device for measuring the resistance between the active surfaces of the at least two electrodes of the neutral electrode when the cover film is attached;
   a decoding device configured to determine a type of the neutral electrode on the basis of the resistance value that is measured when the cover film is attached; and
   a display and/or recording device to, respectively, display and/or record the type of the neutral electrode determined by the decoding device.

2. The electrosurgical apparatus according to claim 1, wherein the decoding device further comprises a comparator for comparing the measured resistance value with stored resistance values and wherein the decoding device determines the type of the neutral electrode as a type having a stored resistance value that matches the measured resistance value.

3. The electrosurgical apparatus according to claim 1, comprising a display to display the type of electrode determined by the decoding device.

4. The electrosurgical apparatus according to claim 1, comprising a recording device to record the type of electrode determined by the decoding device.

5. The electrosurgical apparatus according to claim 1, further comprising a current limiting device for setting a maximum current value to be delivered by the electrosurgical appliance based on the presence of a particular measured resistance.

6. The electrosurgical apparatus according to claim 1, further comprising a current limiting device for setting a maximum current value to be delivered by the electrosurgical appliance based on the type of electrode determined by the decoding device.

7. A method for using a neutral electrode that includes at least two electrodes electrically insulated from each other and having active surfaces for application to a skin segment of a patient, and a cover film having a known electrical resistance attached to the active surfaces in such a way that said surfaces are electrically connected to each other by means of the cover film, the method comprising:
   connecting the neutral electrode to an electrosurgical generator;
   determining a resistance between the at least two electrodes by means of a resistance-measuring device;
   comparing the determined resistance value with stored resistance values;
   selecting a type of the neutral electrode on the basis of the comparison;
   adjusting at least one operating parameter of the generator to correspond to the type of the neutral electrode; and
   removing the cover film and applying the neutral electrode to the skin segment.

8. A method according to claim 7, wherein one of the at least one operating parameters that is adjusted is a maximum current value.

\* \* \* \* \*